United States Patent
Assaker et al.

(10) Patent No.: US 6,652,525 B1
(45) Date of Patent: Nov. 25, 2003

(54) ANTERIOR IMPLANT FOR THE SPINE

(75) Inventors: Richard Assaker, Belgique (FR); Richard-Laurent Minfelde, Paris (FR); Jean-Francois D'Amore, Montevrain (FR)

(73) Assignee: Sofamor S.N.C., CDG Cedex (FR)

( * ) Notice: Subject to any disclaimer, the term of this patent is extended or adjusted under 35 U.S.C. 154(b) by 366 days.

(21) Appl. No.: 09/692,894

(22) Filed: Oct. 20, 2000

Related U.S. Application Data

(63) Continuation of application No. PCT/IB99/00794, filed on Apr. 30, 1999.

(30) Foreign Application Priority Data

Apr. 30, 1998 (FR) .............................. 98 05558

(51) Int. Cl.[7] .............................................. A61B 17/70
(52) U.S. Cl. ........................................ 606/61; 606/70
(58) Field of Search .............................. 606/60, 61, 69, 606/70, 71, 73

(56) References Cited

U.S. PATENT DOCUMENTS

| | | |
|---|---|---|
| 4,408,601 A | 10/1983 | Wenk |
| 4,488,543 A | 12/1984 | Tornier |
| 4,503,848 A | 3/1985 | Caspar et al. |
| 5,057,111 A | 10/1991 | Park |
| 5,108,395 A | 4/1992 | Laurain |
| 5,127,914 A | 7/1992 | Calderale et al. |
| 5,324,290 A | 6/1994 | Zdeblick et al. |
| 5,364,399 A | 11/1994 | Lowery et al. |
| 5,423,826 A | 6/1995 | Coates et al. |
| 5,487,743 A | 1/1996 | Laurain et al. |
| 5,578,034 A | 11/1996 | Estes |
| 5,616,142 A | 4/1997 | Yuan et al. |
| 5,616,144 A | 4/1997 | Yapp et al. |
| 5,620,443 A | 4/1997 | Gertzbein et al. |
| 5,676,666 A | 10/1997 | Oxland et al. |
| 5,904,683 A | 5/1999 | Pohndorf et al. |
| 5,951,558 A | 9/1999 | Fiz |
| 6,017,345 A | 1/2000 | Richelsoph |
| 6,139,550 A | 10/2000 | Michelson |
| 6,152,927 A | 11/2000 | Farris et al. |
| 6,193,721 B1 | 2/2001 | Michelson |
| 6,224,602 B1 | 5/2001 | Hayes |
| 6,235,034 B1 | 5/2001 | Bray |
| 6,258,089 B1 | 7/2001 | Campbell et al. |

FOREIGN PATENT DOCUMENTS

| | | | |
|---|---|---|---|
| EP | 0 599 640 A1 | 6/1994 | |
| EP | 0 705 572 A2 | 10/1996 | ........... A61B/17/70 |
| FR | 2 740 321 A1 | 4/1997 | |
| GB | 780652 | 8/1957 | |
| WO | WO 99/04718 | 2/1999 | |

*Primary Examiner*—David O. Reip
(74) *Attorney, Agent, or Firm*—Woodard, Emhardt, Moriarty, McNett & Henry LLP

(57) ABSTRACT

Implant for the cervical spine comprising an anterior plate (1) for maintaining a bone graft, bone anchorage screws (6, 7, 8) for the plate and at least one slide (22) for blocking the screws and preventing any migration of the screws, characterized in that the at least one slide (22) is slidably mounted on the plate so as to be applicable on at least one anchorage screw head (15, 16). The slide cooperates with boss and recess portions for retaining the slide on the head of the screw. The slide may be formed by a thin platelet (22a)) which is provided with lateral flanges (25) and is slidable in a complementary cavity (18) provided in the plate (1) while being flush with the surface of the plate (1). The plate (1) includes ramps (26) for retaining the slide (22) on which the flanges (25) are slidable, the slide (22) being slidable to a position in which it at least partly overlaps the heads of the associated screws (6 or 7) and is locked in position by suitable structure.

28 Claims, 4 Drawing Sheets

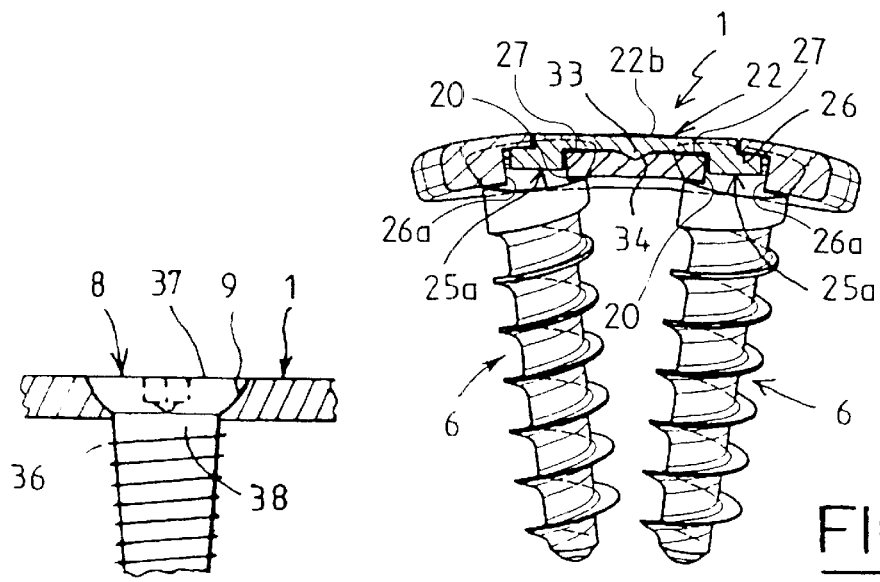
FIG.6
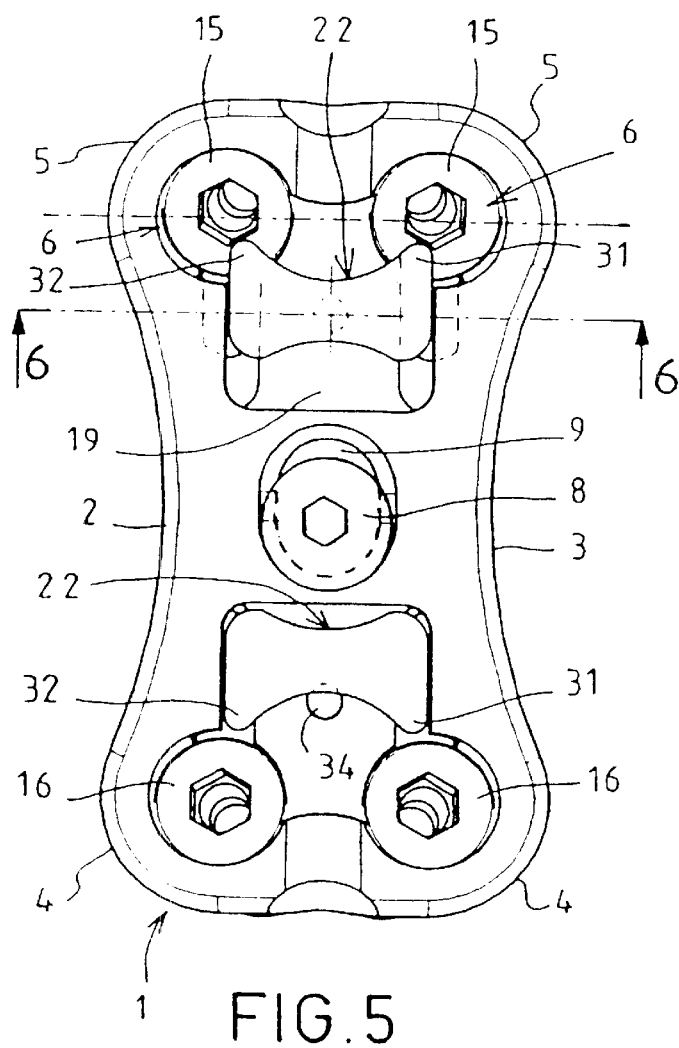
FIG.7
FIG.5

ANTERIOR IMPLANT FOR THE SPINE

CROSS-REFERENCE TO RELATED APPLICATIONS

The present application is a continuation of International Patent Application Number PCT/IB99/00794 filed Apr. 30, 1999.

TECHNICAL FIELD

The present invention relates to an implant for the spine, and more particularly, but not exclusively relates to an anterior plate for maintaining a bone graft, bone anchorage screws for the plate and means for blocking the screws and preventing any migration of the latter.

BACKGROUND

Spinal plates may be introduced from the anterior to stabilize the cervical spine and maintain in position or secure a bone graft which fills the spaces left by the extraction of at least one vertebral disc and, possibly, part of a contiguous cervical vertebra.

The bone anchorage screws used for fixing this type of plate in position are either unicortical, and therefore short, since they pass through only the anterior cortical of the vertebra, or bicortical, and therefore long, since they extend through the anterior cortical and the posterior cortical. The short unicortical screws utilize a locking element when there is a possibility the screws may back-out. On the other hand, the long bicortical screws, while less likely to unscrew, have other limitations making them less desirable in certain situations.

In practice, the locking element employed up to the present time for unicortical screws is an additional screw which is positioned between two bone anchorage screws and whose head overlaps the heads of these two screws. While there are thin cervical plates without a locking element, the addition of an existing locking element to a given plate design typically results in an increase in plate size, such as the plate's thickness. These additions may also result in a greater plate width than is desirable. Thus, the general desire to further decrease the size of surgical implants indicates a need for new plate and/or locking element arrangements.

DISCLOSURE OF THE INVENTION

Accordingly, one object of the present invention is to provide a unique device for stabilizing a patient's spine.

Additionally or alternatively, another object of the invention is to provide an anterior cervical plate provided with antimigration means for the screws arranged in such manner as to avoid increasing the overall size of the plate.

One form of the present invention is a unique device for stabilizing a patient's spine. In a further form, a slide is incorporated into a spinal plate that may be operable to serve as a locking element.

According to another form of the invention, a plate has means for blocking the bone anchorage screws that comprises at least one slide slidably mounted on the plate so as to be capable of partially covering at least one anchorage screw head, and the slide cooperates with means for retaining it on the head of the screw.

In still another form, the slide is formed by a thin platelet provided with at least one flange and slidable in a complementary cavity provided on the surface of the plate, the cavity having a ramp on which the flange can be engaged; the retaining means are formed by a boss on the plate which clicks into an associated recess when the slide is in its position for blocking and locking the screw. The cavity and the platelet may be so dimensioned that the surface of the platelet is flush with that of the plate when it is placed in its cavity. Consequently, for this form, the overall thickness of the anterior plate may not be increased by the slide.

Further forms, embodiments, objects, aspects and features of the invention will be apparent from the following description and the accompanying drawings.

BRIEF DESCRIPTION OF THE DRAWINGS

FIG. 5 is a top view to a larger scale of the anterior plate of FIGS. 1–3 provided with two screw locking slides, one of these slides being in the locking position, while the other is in the withdrawn position before locking.

FIG. 6 is a cross-sectional view taken on line 6—6 of FIG. 5.

FIG. 7 is a partial cross-sectional view taken on line 7—7 of FIG. 3.

MODE(S) FOR CARRYING OUT THE INVENTION

Figure 1:
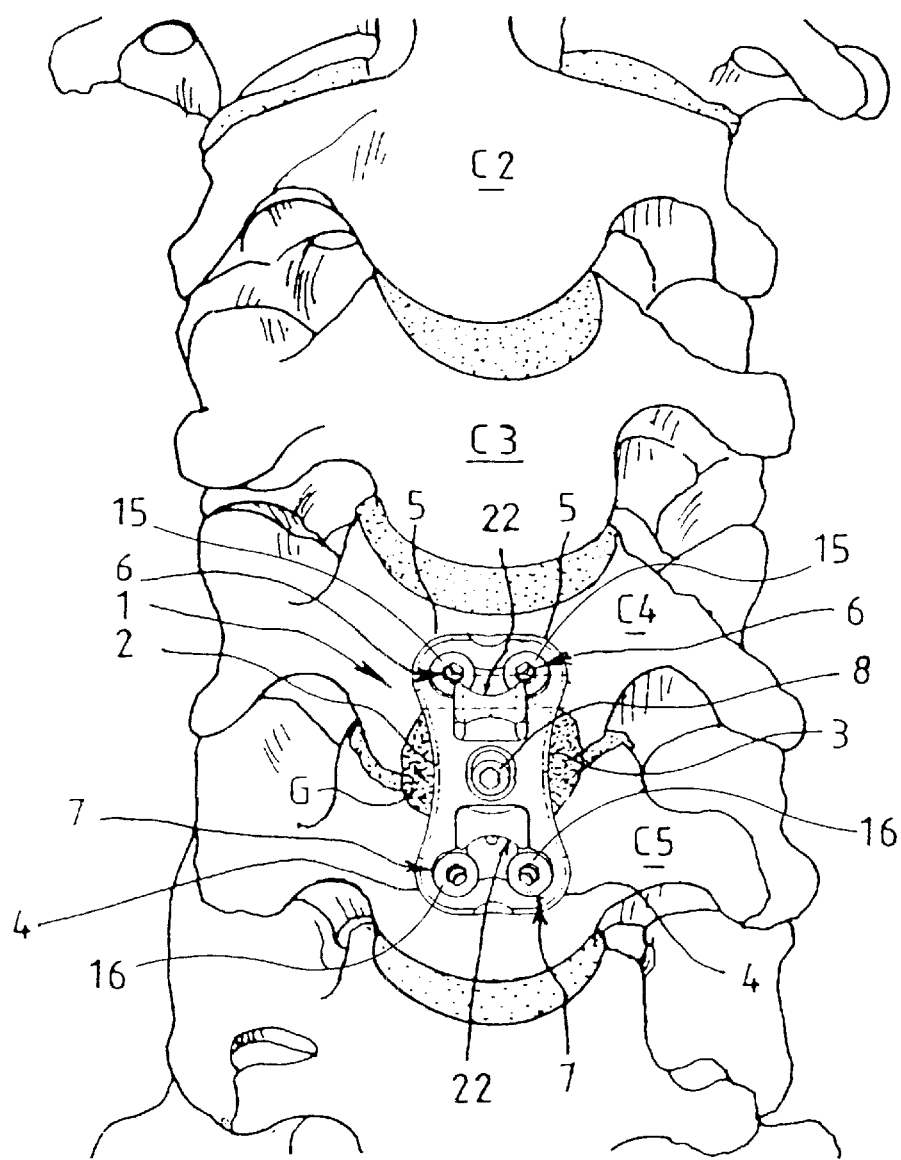
FIG. 1 is an elevation view of a cervical spine segment provided with an anterior implant according to the invention for maintaining a bone graft in position.

For the purposes of promoting an understanding of the principles of the invention, reference will now be made to the embodiments illustrated in the drawings and specific language will be used to describe the same. It will nevertheless be understood that no limitation of the scope of the invention is intended. Any alterations and further modifications in the illustrated or described embodiments, and any further applications of the principles of the invention as described or illustrated therein being contemplated as would normally occur to one skilled in the art to which the invention relates.

Shown in FIG. 1 is a cervical spine segment C2, C3, C4, C5, and between the vertebrae C4 and C5 (more usually C4 and C5) of which a bone graft G (partially visible) is disposed, this graft G being covered by an anterior plate 1 whose function is to stabilize the spine and to maintain this bone graft G in position.

Figure 2:
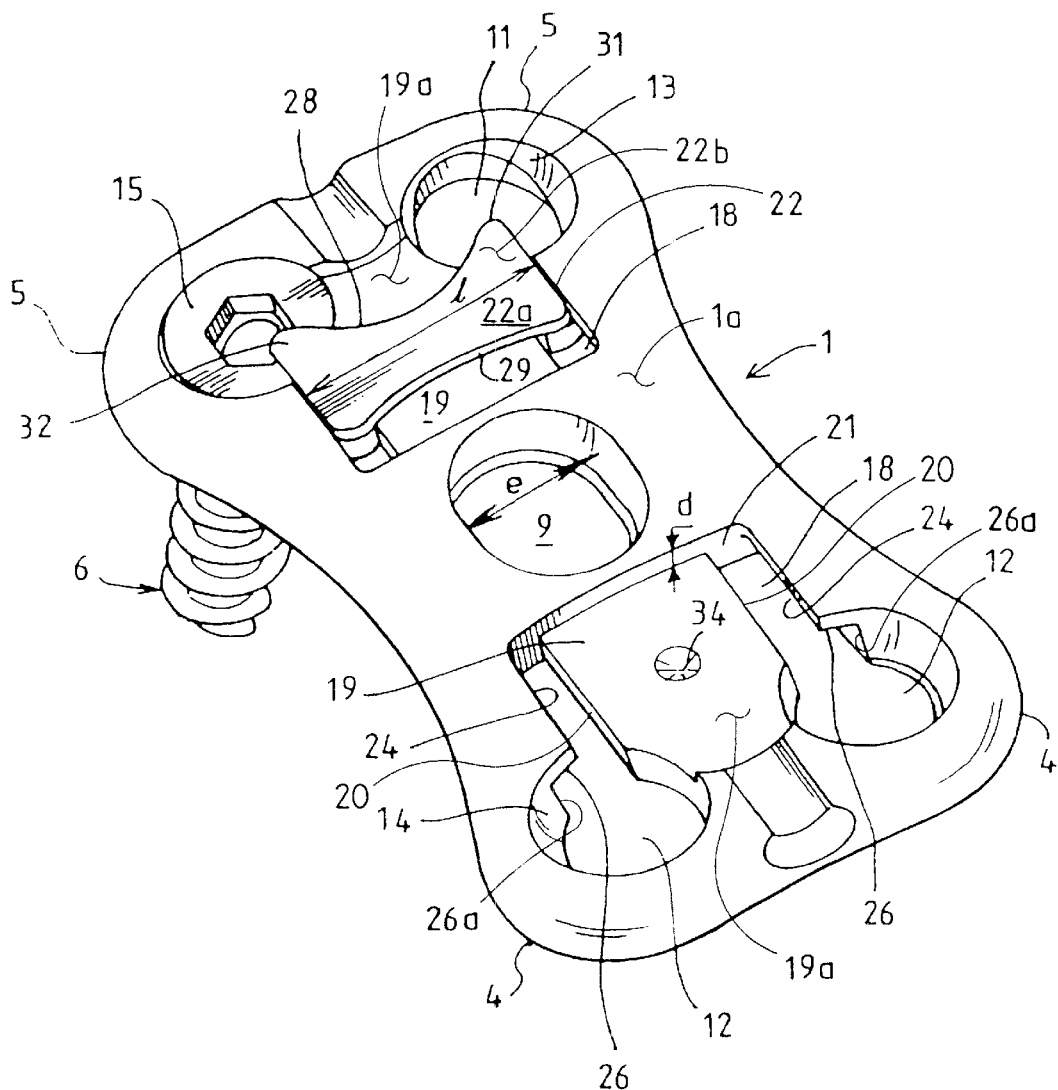
FIG. 2 is a perspective view, to a larger scale, of the anterior plate of FIG. 1 provided with a slide for locking two of the screws of the plate.

Referring additionally to FIG. 2, the plate 1 has an elongate shape with two large concave sides 2, 3 connected to rounded ends 4, 5, these large sides 2, 3 extend from the vertebra C4 to the vertebra C5. The plate 1 is provided adjacent to each of its ends 4, 5 with a pair of bone anchorage screws 6, 7 at C4 and C5 which are unicortical and therefore short, and a central screw 8 which is engaged in an oblong opening 9. Each of the screws 6, 7 extends through a corresponding opening 11, 12 which is of generally circular section but has a spherical wall 13, 14 acting as a bearing surface for the corresponding head 15, 16 of screws 6, 7.

Each pair of openings 11 and 12 opens onto a respective cavity 18 provided in the adjacent surface 1a of the plate 1.

Formed in this cavity 18, which in the presently-described embodiment opens onto the opposite faces of the plate 1, is a bridge 19 which defines at one end a part of the circumference of the openings 11,12 and extends from the latter to the opposite wall 21 of the cavity 18. However, the thickness of each bridge 19 is less than that of the plate 1 so that the surface 19a of each bridge 19 is situated within the cavity 18 at a distance d from the surface 1a of the plate 1 (FIG. 2).

Figure 3:
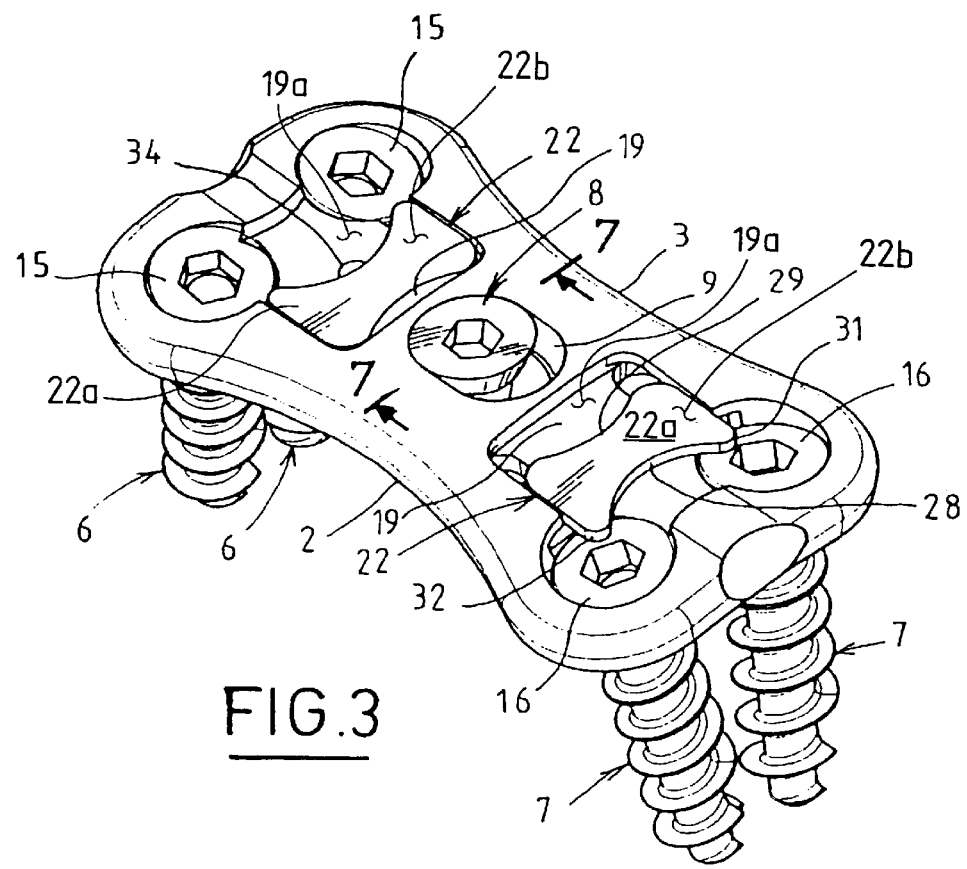
FIG. 3 is a perspective view, similar to FIG. 2, showing the plate provided with two slides and two pairs of bone anchorage screws.
Figure 4:
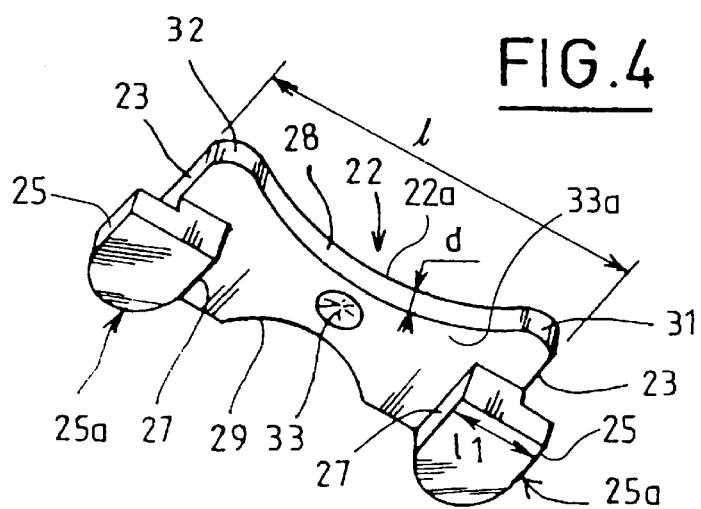
FIG. 4 is a bottom perspective view, to a larger scale, of one of the screw-blocking slides for the anterior plate of FIGS. 1–3.

Each pair of bone anchorage screws 6, and each pair of screws 7, is associated with a slide 22 for locking screws 6, 7 after anchorage in the vertebral bodies C4, C5, respectively; and thereby preventing migration of the screws 6, 7. Referring further to FIGS. 3 and 4, each slide 22 is formed by a thin platelet 22a whose thickness is at the most about equal to the distance d between the upper surface 1a of the plate 1 and the surface 19a of the bridge 19. This platelet 22a has an elongate shape whose larger dimension $l$ is just equal to the width of the cavity 18 to allow insertion of the platelet 22a in the latter. Each platelet 22a, not cambered in the free state, is generally slightly cambered in order to make it possible to insert it into its housing cavity 18. This insertion is carried out by positioning it on the bridge 19 and applying a force such that its opposite sides 23 slidably and resiliently bear against the retaining ramps 26. Retaining ramps 26 are each defined along a corresponding one of the opposite sides 24 of cavity 18.

Further, each platelet 22a is provided with two lateral flanges 25 which project from the sides 23 under the central part of the platelet 22a. Each of the flanges 25 is adapted to form a shoe 25a slidable along a respective retaining ramp 26 (FIGS. 2 and 6). The flanges 25 have a width $l$ allowing their insertion in the slots 26a between the sides 24 of the cavity 18 and the opposing sides 20 of the bridge 19, so that their inner faces 27 are placed in sliding contact with the sides 20 of the bridge 19 (FIG. 6) when the platelet 22a has been placed in position.

The two large sides 28, 29 of each platelet 22a are concave and the apices 31, 32 of each platelet 22a are rounded so that the rounded apices 31, 32 of the sides 28 close to the screws 6 or 7 are able to partly overlap the heads 15, 16 of the screws 6, 7 when the platelets 22a are in position for locking the screws 6, 7 (FIGS. 1, 2, 5, 6). Indeed, the openings 11, 12 and the heads 15, 16 are so arranged that, when the screws 6, 7 have been screwed into the vertebral bodies with possibly an inclination in regard to plate 1, their heads 15, 16 have their surfaces in a position in which they are just flush with the underside of the round apices 31, 32.

Referring more specifically to FIGS. 2–6, means are provided for retaining the platelets 22a in their position for locking the screws 6, 7. In the presently-described embodiment, these means comprise, for each platelet 22a, a central boss 33 projecting from the lower face 33a of the platelet 22a, namely that placed in contact with the surface 19a of the support bridge 19, and a corresponding recess 34 provided in the central part of the bridge 19. Thus, when the platelet 22a reaches the position for locking the screws 6, 7; its boss 33 clicks into the recess 34 and maintains the platelet 22a in this position and prevents it from moving forwardly or rearwardly in its cavity 18.

Referring next to FIGS. 2, 3, 5, and 7, the first thread 36 of the central screw 8 (i.e., the thread closest to its head 37, See FIG. 7) is separated from the latter by a smooth part 38. The diameter of this first thread 36 is larger than that of the smooth part 38 and the width e of the oblong opening 9 arranged to receive screw 8 (See FIG. 2). To place the screw 8 in position, it is therefore necessary to force it through the opening 9 and cause the latter to pass beyond the first thread 36. Thereafter, the latter performs the function of means for retaining screw 8 in plate 1.

To place the plate 1 and its locking slides 22 in position on the cervical segment such as C4, C5 of FIG. 1, the procedure is the following. Referring generally to FIGS. 1–7, first of all, after the bone graft G has been placed in position in the discal space previously prepared, the surgeon positions the plate 1 equipped with slides 22 and attaches it by means of screws 6 and 7. Afterwards he makes each slide 22 run from the bottom of its housing cavity 18 until flanges 25 come and stop against screws heads 15 and 16. The latter are then partially covered by rounded tops 31, 32 as shown in FIGS. 1, 2, 3, and 5 for at least one of slides 22. When the slides 22 reach this position, in which they partly overlap the heads 15, 16; their respective boss 33 clicks into the respective recess 34 so that each slide 22 is locked in this position in which it locks the associated screws 15, 16 against any migration and therefore against any posterior movement.

As can be seen in FIG. 6, the slides 22 do not project above the surface of the plate 1 owing to their small thickness which is at the maximum equal to about d and to the provision of a suitable cavity 18. Thus the surface 22b of the slides 22 is generally flush with surface 1a of the plate 1 whose overall thickness is consequently not increased by the presence of the locking slides 22. The locking platelets 22a do not impose to increase the width of the plate 1 in respect to its minimum width such that the same results from the chosen gap between the axis of screws 6 and 7.

It should be appreciated that the scope of the invention is not intended to be limited to the described embodiments and may encompass variants. For example, boss 33 can be formed on support 19 whilst recess 34 is formed on the platelet 22a. Thus the means 33, 34 for blocking the slides 22 in their locking position may be replaced by any other like system. Further, in another arrangement, a slide is associated with each screw and has a single flange that is suitably dimensioned for this purpose. Optionally, the plate may be provided with only a single blocking slide 22, the second pair of screws being for example associated with other blocking means, or being absent. Moreover, in further embodiments, the implant according to the invention can be used, not only for the cervical spine, but also for other spine segments, for example thoracic and lumbar, and possibly without any bone grafts. Further, in other embodiments, the screw-locking slide and plate arrangement may be used to reduce undesired migration of one or more screws of a type other than the unicortical variety; and may be used to check undesired migration of other types of fasteners used in addition to or as an alternative to one or more screws.

In one alternative embodiment of the present invention, an implant for the spine includes an anterior plate for stabilizing the spine and maintaining a bone graft that has a number of openings, a number of bone anchorage screws for correspondingly engaging the openings of the plate, and means for blocking the screws and preventing any migration of the screws. This implant is further characterized in that the blocking means comprises at least one slide slidably mounted on the plate so as to be capable of partially covering at least one anchorage screw head. This slide cooperates with means for retaining the slide on the head of the screw.

In further embodiment, an implant for the spine includes: a plate for stabilizing the spine that has a number of openings; a number of bone anchorage screws each operable to engage a corresponding one of the openings of the plate; and means for blocking the screws and preventing screw migration. The blocking means includes at least one slide slidably mounted on the plate to selectively cover at least a part of at least one of the screws and means for retaining the slide on at least one of the screws.

In an additional embodiment, an implant for the spine includes: a plate for stabilizing the spine that comprises a number of openings and defines a cavity adjacent at least one of the openings; a number of bone anchorage screws each operable to pass through a corresponding one of the openings of the plate to engage the spine; and a slide slidably mounted in the cavity of the plate. The slide is operable to selectively cover at least a portion of at least one of the screws mounted in at least one of the openings.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. An implant for the spine comprising an anterior plate for stabilizing the spine and maintaining a bone graft, the plate having a number of openings, a number of bone anchorage screws for correspondingly engaging the openings of the plate, and means for blocking the screws and preventing any migration of the screws, characterized in that the blocking means comprise at least one slide slidably mounted on the plate so as to be capable of partially covering at least one anchorage screw head, and the slide cooperates with means for retaining the slide on the head of the screw, wherein the slide is formed by a platelet including at least one flange and the plate defines a cavity with at least one ramp to engage the at least one flange and retain the platelet on the plate.

2. The implant according to claim 1, characterized in that the retaining means comprises a boss on the slide which is clicked into a corresponding recess defined by a bridge of the plate when the slide is in a position for blocking the screws.

3. The implant according to claim 1, characterized in that the platelet is provided with two lateral flanges each adapted to slide along a corresponding one of two ramps, the ramps retaining the platelet in the cavity and being formed on opposite sides of the cavity, the platelet being cambered to allow the platelet to be resiliently inserted in the cavity, and the platelet is dimensioned for at least partially overlapping a pair of screw heads each belonging to a corresponding one of the bone anchorage screws.

4. The implant according to claim 1, characterized in that the cavity and the platelet are so dimensioned that the surface of the platelet is generally flush with a surface of the plate when the platelet is placed in the cavity.

5. The implant according to claim 1, characterized in that the plate defines another cavity arranged to receive another slide slidably mounted to the plate.

6. The implant according to claim 1, characterized in that the cavity communicates with a pair of the openings of the plate.

7. The implant according to claim 6, wherein a central part of the plate defines a central opening and further comprising a selected bone anchorage screw to pass through the central opening, the selected bone anchorage screw including a first thread and a screw head, the first thread being separated from the screw head by a generally smooth part, the first thread having a diameter larger than the width of the screw passage opening for preventing the return of the selected bone anchorage screw after the bone anchorage screw is inserted in through the central opening.

8. An implant for the spine, comprising:
a plate for stabilizing the spine, the plate having a number of openings;
a number of bone anchorage screws each operable to engage a corresponding one of the openings of the plate;
means for blocking the screws including at least one slide mounted on the plate to selectively cover at least a part of at least one of the screws and means for retaining the slide on at least one of the screws, the slide cooperating with the retaining means; and
wherein the slide is formed by a platelet including at least one flange, and the retaining means includes at least one ramp defined by the plate to engage the at least one flange and retain the platelet on the plate.

9. The implant according to claim 8, wherein the retaining means comprises a boss on the slide which is clicked into a corresponding recess defined by a bridge of the plate when the slide is in a position for blocking the screws.

10. The implant according to claim 8 wherein the slide includes a platelet, the platelet includes two lateral flanges each adapted to slide along a corresponding one of two ramps formed on opposite sides of the cavity, and the platelet is dimensioned to at least partially overlap a pair of screw heads each belonging to a corresponding one of the bone anchorage screws.

11. The implant according to claim 8, wherein the plate defines a cavity and the slide is mounted within the cavity.

12. The implant according to claim 11, wherein the cavity communicates with a pair of the openings of the plate.

13. The implant according to claim 12, herein a central part of the plate defines a central opening and further comprising a selected bone anchorage screw to pass through the central opening, the selected bone anchorage screw including a first thread and a screw head, the first thread being separated from the screw head by a generally smooth part, the first thread having a diameter larger than the width of the screw passage opening.

14. The implant according to claim 8, wherein the platelet includes a platelet surface, and the platelet surface is generally flushed with a surface of the plate when the platelet is placed in the cavity.

15. The implant according to claim 8, wherein the plate defines another cavity arranged to receive another slide mounted to the plate.

16. An implant for the spine, comprising:
a plate for stabilizing the spine, the plate including a number of openings and defining a cavity;
a number of bone anchorage screws each operable to pass through a corresponding one of the openings of the plate to engage the spine;
a slide mounted in the cavity of the plate, the slide being operable to selectively cover at least a portion of at least one of the screws mounted in the corresponding one of the openings; and
wherein the slide includes a platelet with a first flange adapted to slide along a first ramp formed along a first side of the cavity to retain the platelet in the cavity.

17. The implant according to claim 16, wherein the plate includes a bridge adjacent the slide, and one of the bridge and the slide includes a boss and another of the bridge and the slide includes a recess to correspondingly receive the boss to retain the slide in a screw retaining position.

18. The implant according to claim 17, herein the platelet includes a surface that is generally flush with a surface of the plate when the platelet is placed in the cavity.

19. The implant according to claims 17, wherein the cavity communicates with a pair of the openings of the plate.

20. The implant according to claim 17, wherein a central part of the plate defines a central opening and further comprising a selected bone anchorage screw to pass through the central opening, the selected bone anchorage screw including a first thread and a screw head, the first thread being separated from the screw head by a generally smooth part, the first thread having a diameter larger than the width of the screw passage opening.

21. The implant according to claim 17, further comprising another slide received in another cavity defined by the plate.

22. The implant according to claim 16, wherein the platelet includes a second flange opposite the first flange to slide along a second ramp formed along a second side of the cavity, the second side being opposite the first side.

23. An implant for the spine, comprising:
  a plate for stabilizing the spine, the plate including a number of openings with a central part defining a central one of the openings;
  a number of bone anchorage screws each operable to engage a corresponding one of the openings of the plate;
  means for blocking the screws including at least one slide mounted on the plate to selectively cover at least a part of at least one of the screws and means for retaining the slide on at least one of the screws; and
  wherein the plate defines a cavity that communicates with a pair of the openings through the plate, the slide is mounted in the cavity, one of the bone anchorage screws is operable to pass through the central one of the openings, and the one of the bone anchorage screws includes a thread and a screw head with the thread being separated from the screw head by a generally smooth part and with the thread having a diameter larger than the width of the screw passage opening.

24. The implant according to claim 23, wherein the retaining means comprises a boss on the slide which is clicked into a corresponding recess defined by a bridge of the plate when the slide is in a position for blocking the screws.

25. The implant according to claim 23, wherein the slide includes a platelet, the platelet includes two lateral flanges each adapted to slide along a corresponding one of two ramps formed on opposite sides of the cavity, and the platelet is dimensioned to at least partially overlap a pair of screw heads each belonging to a corresponding one of the bone anchorage screws.

26. An implant for the spine, comprising:
  a plate for stabilizing the spine, the plate including a number of openings and defining a cavity, a central portion of the plate defining one of the openings;
  a number of bone anchorage screws each operable to pass through a corresponding one of the openings of the plate to engage the spine, one of the screws being sized to pass through the one of the openings and including a thread and a screw head, the thread being separated from the screw head by a generally smooth part, the thread having a diameter larger than the width of the screw passage opening;
  a slide mounted in the cavity of the plate, the slide being operable to selectively cover at least a portion of at least one of the screws mounted in the corresponding one of the openings; and
  wherein the plate includes a bridge adjacent the slide, and one of the bridge and the slide includes a boss and another of the bridge and the slide includes a recess to correspondingly receive the boss to retain the slide in a screw retaining position.

27. The implant according to claim 26, wherein the slide is formed by a platelet including at least one flange, the cavity includes at least one ramp to engage the at least one flange and retain the platelet on the plate.

28. The implant according to claim 26, wherein the platelet includes a surface that is generally flush with a surface of the plate when the platelet is placed in the cavity.

* * * * *